(12) United States Patent
Sato et al.

(10) Patent No.: US 9,701,739 B2
(45) Date of Patent: Jul. 11, 2017

(54) MONOCLONAL ANTIBODY HAVING IMMUNOSUPPRESSIVE ACTIVITY OR ANTIGEN BINDING FRAGMENT THEREOF

(75) Inventors: Shuji Sato, Narita (JP); Takeshi Goto, Ushiku (JP); Shigeru Goto, Beppu (TW); Toshiaki Nakano, Kaohsiung (TW); Naoya Ohmori, Chiba (JP); Kueichen Chiang, Tokyo-to (JP); Yayoi Shimada, Kisarazu (JP); Kenji Mori, Ryugasaki (JP); Takamitsu Miyagi, Sodegaura (JP)

(73) Assignee: Josai University Corporation, Tokyo-to (JP)

( * ) Notice: Subject to any disclaimer, the term of this patent is extended or adjusted under 35 U.S.C. 154(b) by 987 days.

(21) Appl. No.: 13/817,714

(22) PCT Filed: Aug. 19, 2011

(86) PCT No.: PCT/JP2011/068793
§ 371 (c)(1),
(2), (4) Date: Aug. 12, 2013

(87) PCT Pub. No.: WO2012/023614
PCT Pub. Date: Feb. 23, 2012

(65) Prior Publication Data
US 2014/0010815 A1 Jan. 9, 2014

(30) Foreign Application Priority Data
Aug. 20, 2010 (JP) .................. 2010-185406

(51) Int. Cl.
*A61K 39/395* (2006.01)
*C07K 16/18* (2006.01)
*C07K 7/08* (2006.01)

(52) U.S. Cl.
CPC ........ *C07K 16/18* (2013.01); *A61K 39/39541* (2013.01); *C07K 7/08* (2013.01); *C07K 2317/34* (2013.01)

(58) Field of Classification Search
None
See application file for complete search history.

(56) References Cited

U.S. PATENT DOCUMENTS

| 8,187,602 | B2 | 5/2012 | Goto et al. |
| 8,716,218 | B2 | 5/2014 | Esmon et al. |
| 2004/0052780 | A1 | 3/2004 | Ono et al. |
| 2008/0287352 | A1 | 11/2008 | Goto et al. |
| 2009/0081247 | A1 | 3/2009 | Sato et al. |
| 2009/0117099 | A1 | 5/2009 | Esmon et al. |
| 2009/0252751 | A1 | 10/2009 | Sato et al. |
| 2010/0196384 | A1 | 8/2010 | Goto et al. |
| 2010/0324469 | A1 | 12/2010 | Mori et al. |
| 2015/0079090 | A1 | 3/2015 | Sato et al. |

FOREIGN PATENT DOCUMENTS

| CN | 101056979 A | 10/2007 |
| EP | 1820855 A1 | 8/2007 |
| EP | 2196212 A1 | 6/2010 |
| JP | 2004-149507 A | 5/2004 |
| JP | 2011-503012 A | 1/2011 |
| WO | WO-92/11029 A1 | 7/1992 |
| WO | WO-2006/025580 A1 | 3/2006 |
| WO | WO-2009/001673 A1 | 12/2008 |
| WO | WO-2009/044555 A1 | 4/2009 |
| WO | WO-2012/023614 A1 | 2/2012 |
| WO | WO-2013/008171 A1 | 1/2013 |

OTHER PUBLICATIONS

MacCallum et al. " Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Chiang et al., "A novel peptide mimotope identified as a potential immunosuppressive vaccine for organ transplantation," J Immunol. 182(7):4282-4288 (2009).
Rekvig et al., "Human autoantibodies that react with both cell nuclei and plasma membranes display specificity for the octamer of histones H2A, H2B, H3, and H4 in high salt," J Exp Med. 152(6):1720-1733 (1980).
Shimada et al., "Development of a two-step chromatography procedure that allows the purification of a high-purity anti-histone H1 monoclonal immunoglobulin M antibody with immunosuppressant activity," Biomed Chromatogr. 22(1):13-19 (2008).
Takaoka et al., "Unexpected T cell regulatory activity of anti-histone H1 autoantibody: Its mode of action in regulatory T cell-dependent and -independent manners," Biochem Biophys Res Commun. 431(2):246-252 (2013).
Chaput et al., "Sepsis: the dark side of histones," Nat Med. 15(11):1245-6 (2009).
Fuchs et al., "Histones induce rapid and profound thrombocytopenia in mice," Blood. 118(13):3708-14 (2011).
Huang et al., "Endogenous histones function as alarmins in sterile inflammatory liver injury through Toll-like receptor 9 in mice," Hepatology. 54(3):999-1008 (2011).
International Preliminary Report on Patentability for International Application No. PCT/JP2011/068793, "Monoclonal Antibody Having Immunosuppressive Activity or Fragment to Which Antigen Thereof is Bonded" Sato, Shuji; Goto, Takeshi; Goto, Shigeru; Nakano, Toshiaki; Ohmori, Naoya; Chiang, Kueichen; Shimada, Yayoi; Mori, Kenji; Miyagi, Takamitsu, filed on Aug. 19, 2011, mailed Jul. 18, 2012 (17 pages).

(Continued)

*Primary Examiner* — Ron Schwadron
(74) *Attorney, Agent, or Firm* — Clark & Elbing LLP; Susan M. Michaud

(57) ABSTRACT

The present invention relates to a monoclonal antibody having excellent immunosuppressive activity or an antigen binding fragment thereof. More specifically, the present invention relates to a monoclonal antibody or an antigen binding fragment thereof, which binds to a peptide consisting an amino acid sequence represented by SSVLYGG-PPSAA (SEQ ID NO: 1) or a conjugate of the peptide and a pharmaceutically acceptable carrier, the monoclonal antibody or an antigen binding fragment thereof having a higher binding affinity for core histone than for histone H1.

10 Claims, 6 Drawing Sheets

(56) References Cited

OTHER PUBLICATIONS

International Preliminary Report on Patentability for International Application No. PCT/JP2013/054551, "Therapeutic Agent for Inflammatory Disease", Sato, Shuji; Takeshi, Goto; Ohmori, Naoya; Chiang, Kueichen; Shimada, Yayoi; Inomata, Masafumi; Kusano, Toru; Hiratsuka Takahiro; Noguchi, Takayuki; Hagiwara, Satoshi, filed Feb. 22, 2013, mailed Aug. 28, 2014 (7 pages).
International Search Report for International Application No. PCT/JP2013/054551, "Therapeutic Agent for Inflammatory Disease," Sato, Shuji; Takeshi, Goto; Ohmori, Naoya; Chiang, Kueichen; Shimada, Yayoi; Inomata, Masafumi; Kusano, Toru; Hiratsuka Takahiro; Noguchi, Takayuki; Hagiwara, Satoshi, filed Feb. 22, 2013, mailed Apr. 2, 2013 (8 pages).
Japanese Office Action for Japanese Patent Application No. 2012-529630, "Monoclonal Antibody Having Immunosuppressive Activity or Fragment to Which Antigen Thereof is Bonded" Sato, Shuji; Goto, Takeshi; Goto, Shigeru; Nakano, Toshiaki; Ohmori, Naoya; Chiang, Kueichen; Shimada, Yayoi; Mori, Kenji; Miyagi, Takamitsu, filed on Aug. 19, 2011, dated Sep. 25, 2015 (10 pages).
Japanese Office Action for Japanese Patent Application No. 2012-529630, "Monoclonal Antibody Having Immunosuppressive Activity or Fragment to Which Antigen Thereof is Bonded" Sato, Shuji; Goto, Takeshi; Goto, Shigeru; Nakano, Toshiaki; Ohmori, Naoya; Chiang, Kueichen; Shimada, Yayoi; Mori, Kenji; Miyagi, Takamitsu, filed on Aug. 19, 2011, mailed Feb. 5, 2016 (5 pages).
Japanese Office Action for Japanese Patent Application No. 2012-529630, "Monoclonal Antibody Having Immunosuppressive Activity or Fragment to Which Antigen Thereof is Bonded" Sato, Shuji; Goto, Takeshi; Goto, Shigeru; Nakano, Toshiaki; Ohmori, Naoya; Chiang, Kueichen; Shimada, Yayoi; Mori, Kenji; Miyagi, Takamitsu, filed on Aug. 19, 2011, mailed Jan. 5, 2016 (5 pages).
Kusano et al., "A novel anti-histone H1 monoclonal antibody, SSV monoclonal antibody, improves lung injury and survival in a mouse model of lipopolysaccharide-induced sepsis-like syndrome," BioMed Res Int. 2015(491649):1-10 (2015).
Office Action for Chinese Patent Application No. 201380020995.1, "Therapeutic Agent for Inflammatory Disease," Sato, Shuji; Takeshi, Goto; Ohmori, Naoya; Chiang, Kueichen; Shimada, Yayoi; Inomata, Masafumi; Kusano, Toru; Hiratsuka Takahiro; Noguchi, Takayuki; Hagiwara, Satoshi, filed Feb. 22, 2013, dated May 19, 2016 (11 pages).
Office Action for European Patent Application No. 13751092.1, "Therapeutic Agent for Inflammatory Disease", Sato, Shuji; Takeshi, Goto; Ohmori, Naoya; Chiang, Kueichen; Shimada, Yayoi; Inomata, Masafumi; Kusano, Toru; Hiratsuka Takahiro; Noguchi, Takayuki; Hagiwara, Satoshi, filed Feb. 22, 2013, dated Jun. 14, 2016 (8 pages).
Office Action in Chinese Patent Application No. 201180045987.3, "Monoclonal Antibody Having Immunosuppressive Activity or Fragment to Which Antigen Thereof is Bonded" Sato, Shuji; Goto, Takeshi; Goto, Shigeru; Nakano, Toshiaki; Ohmori, Naoya; Chiang, Kueichen; Shimada, Yayoi; Mori, Kenji; Miyagi, Takamitsu, filed on Aug. 19, 2011, dated Aug. 29, 2014 (12 pages).
Supplementary European Search Report for European Application No. 13751092.1, "Therapeutic Agent for Inflammatory Disease", Sato, Shuji; Takeshi, Goto; Ohmori, Naoya; Chiang, Kueichen; Shimada, Yayoi; Inomata, Masafumi; Kusano, Toru; Hiratsuka Takahiro; Noguchi, Takayuki; Hagiwara, Satoshi, filed Feb. 22, 2013, dated Jun. 22, 2015 (10 pages).
Supplementary European Search Report for European Application No. EP 11818254.2, "Monoclonal Antibody Having Immunosuppressive Activity or Fragment to Which Antigen Thereof Is Bonded" Sato, Shuji; Goto, Takeshi; Goto, Shigeru; Nakano, Toshiaki; Ohmori, Naoya; Chiang, Kueichen; Shimada, Yayoi; Mori, Kenji; Miyagi, Takamitsu, filed on Aug. 19, 2011, dated Dec. 12, 2013 (10 pages).
Taiwanese Office Action for Taiwanese Patent Application No. 100129738, "Monoclonal Antibody Having Immunosuppressive Activity or Fragment to Which Antigen Thereof is Bonded" Sato, Shuji; Goto, Takeshi; Goto, Shigeru; Nakano, Toshiaki; Ohmori, Naoya; Chiang, Kueichen; Shimada, Yayoi; Mori, Kenji; Miyagi, Takamitsu, filed on Aug. 19, 2011, dated Oct. 15, 2013 (9 pages).
Xu et al., "Extracellular histones are major mediators of death in sepsis," Nat Med. 15(11):1318-21 (2009).
Xu et al., "Extracellular histones are mediators of death through TLR2 and TLR4 in mouse fatal liver injury," J Immunol. 187(5):2626-31 (2011).

\* cited by examiner

SEQUENCE LISTING

<160> NUMBER OF SEQ ID NOS: 13

<210> SEQ ID NO 1
<211> LENGTH: 12
<212> TYPE: PRT
<213> ORGANISM: Artificial
<220> FEATURE:
<223> OTHER INFORMATION: SSV PEPTIDE

<400> SEQUENCE: 1

Ser Ser Val Leu Tyr Gly Gly Pro Pro Ser Ala Ala
1               5                   10

<210> SEQ ID NO 2
<211> LENGTH: 10
<212> TYPE: PRT
<213> ORGANISM: Artificial
<220> FEATURE:
<223> OTHER INFORMATION: SSV Mab- LIGHT CHAIN VARIABLE REGION CDR1

<400> SEQUENCE: 2

Arg Ala Ser Ser Ser Val Ser Tyr Met His
1               5                   10

<210> SEQ ID NO 3
<211> LENGTH: 7
<212> TYPE: PRT
<213> ORGANISM: Artificial
<220> FEATURE:
<223> OTHER INFORMATION: SSV Mab- LIGHT CHAIN VARIABLE REGION CDR2

<400> SEQUENCE: 3

Ala Thr Ser Asn Leu Ala Ser
1               5

<210> SEQ ID NO 4
<211> LENGTH: 9
<212> TYPE: PRT
<213> ORGANISM: Artificial
<220> FEATURE:
<223> OTHER INFORMATION: SSV Mab- LIGHT CHAIN VARIABLE REGION CDR3

<400> SEQUENCE: 4

Gln Gln Trp Ser Ser Asn Pro Trp Thr
1               5

<210> SEQ ID NO 5
<211> LENGTH: 387
<212> TYPE: DNA
<213> ORGANISM: Artificial
<220> FEATURE:
<223> OTHER INFORMATION: SSV Mab- LIGHT CHAIN VARIABLE REGION DNA

<400> SEQUENCE: 5
atggattttc aagtgcagat tttcagcttc ctgctaatca gtgcttcagt cataatgtcc      60
agaggacaaa ttgttctctc ccagtctcca gcaatcctgt ctgcatctcc aggggagaag     120
gtcacaatga cttgcagggc cagctcaagt gtaagttaca tgcactggta ccagcagaag     180
ccaggatcct cccccaaacc ctggatttat gccacatcca acctggcttc tggagtccct     240
gctcgcttca gtggcagtgg gtctgggacc tcttactctc tcacaatcag cagagtggag     300
gctgaagatg ctgccactta ttactgccag cagtggagta gtaacccgtg gacgttcggt     360
ggaggcacca agctggaaat caaacgg                                         387

```
<210> SEQ ID NO 6
<211> LENGTH: 128
<212> TYPE: PRT
<213> ORGANISM: Artificial
<220> FEATURE:
<223> OTHER INFORMATION: SSV Mab- LIGHT CHAIN VARIABLE REGION PRT

<400> SEQUENCE: 6

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Trp Thr Phe Gly Gly Gly Thr Lys Leu Glu Ile Lys
        115                 120                 125

<210> SEQ ID NO 7
<211> LENGTH: 5
<212> TYPE: PRT
<213> ORGANISM: Artificial
<220> FEATURE:
<223> OTHER INFORMATION: SSV Mab- HEAVY CHAIN VARIABLE REGION CDR1

<400> SEQUENCE: 7

Gly Tyr Asn Met Asn
1               5

<210> SEQ ID NO 8
<211> LENGTH: 17
<212> TYPE: PRT
<213> ORGANISM: Artificial
<220> FEATURE:
<223> OTHER INFORMATION: SSV Mab- HEAVY CHAIN VARIABLE REGION CDR2

<400> SEQUENCE: 8

Asn Ile Asn Pro Tyr Tyr Gly Ser Thr Ser Tyr Asn Gln Lys Phe Lys
1               5                   10                  15

Gly

<210> SEQ ID NO 9
<211> LENGTH: 13
<212> TYPE: PRT
<213> ORGANISM: Artificial
<220> FEATURE:
<223> OTHER INFORMATION: SSV Mab- HEAVY CHAIN VARIABLE REGION CDR3

<400> SEQUENCE: 9

Ser Pro Tyr Tyr Ser Asn Tyr Trp Arg Tyr Phe Asp Tyr
1               5                   10

<210> SEQ ID NO 10
<211> LENGTH: 423
<212> TYPE: DNA
<213> ORGANISM: Artificial
```

<220> FEATURE:
<223> OTHER INFORMATION: SSV Mab- HEAVY CHAIN VARIABLE REGION DNA

<400> SEQUENCE: 10

```
atgggatgga gctggatctt tctcttcctt ctgtcagtaa ctgcaggtgt ccactctgag      60
atccagctgc agcagtctgg agctgagctg gtgaagcctg gggcttcagt gaagatatcc     120
tgcaaggctt ctggttactc attcactggc tacaacatga actgggtgaa gcagagccat     180
ggaaagagcc ttgagtggat tggaaatatt aatccttact atggtagtac tagctacaat     240
cagaagttca agggcaaggc cacattgact gtagacaaat cttccagcac agcctacatg     300
cagctcaaca gcctgacatc tgaggactct gcagtctatt actgtgcaag aagtccctac     360
tatagtaact actggaggta ctttgactac tggggccaag gcaccactct cacagtctcc     420
tca                                                                   423
```

<210> SEQ ID NO 11
<211> LENGTH: 141
<212> TYPE: PRT
<213> ORGANISM: Artificial
<220> FEATURE:
<223> OTHER INFORMATION: SSV Mab- HEAVY CHAIN VARIABLE REGION PRT

<400> SEQUENCE: 11

```
Met Gly Trp Ser Trp Ile Phe Leu Phe Leu Leu Ser Val Thr Ala Gly
1               5                   10                  15

Val His Ser Glu Ile Gln Leu Gln Gln Ser Gly Ala Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly Asn Ile Asn Pro Tyr Tyr Gly Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Ser Pro Tyr Ser Asn Tyr Trp Arg Tyr Phe
        115                 120                 125

Asp Tyr Trp Gly Gln Gly Thr Thr Leu Thr Val Ser Ser
    130                 135                 140
```

<210> SEQ ID NO 12
<211> LENGTH: 26
<212> TYPE: DNA
<213> ORGANISM: Artificial
<220> FEATURE:
<223> OTHER INFORMATION: PRIMER

<400> SEQUENCE: 12

```
caccatggag ttagtttggg cagcag                                           26
```

<210> SEQ ID NO 13
<211> LENGTH: 23
<212> TYPE: DNA

```
<213> ORGANISM: Artificial
<220> FEATURE:
<223> OTHER INFORMATION: PRIMER

<400> SEQUENCE: 13
cacgactgag gcacctccag atg                                             23
```

MONOCLONAL ANTIBODY HAVING IMMUNOSUPPRESSIVE ACTIVITY OR ANTIGEN BINDING FRAGMENT THEREOF

CROSS REFERENCE TO RELATED APPLICATIONS

The present application claims priority to Japan Patent Application No. 2010-185406 filed on Aug. 20, 2010, which is hereby incorporated by reference in its entirety.

TECHNICAL FIELD

The present invention relates to a monoclonal antibody having excellent immunosuppressive activity or an antigen binding fragment thereof and a hybridoma that produces them.

BACKGROUND ART

In organ transplantation therapy, conventionally, various immunosuppressive agents are used in order to suppress rejection after organ transplantation. These immunosuppressive agents include, for example, tacrolimus (FK506) and ciclosporin A (Jpn J Pharmacol, 71, 89-100, 1996). However, conventional immunosuppressive agents have disadvantages including intense adverse effects such as growth stimulation of cancer cells and myelosuppression; infectious diseases and even the need of lifelong administration (Nonpatent Literature 1: Transplantation, 58, 170-178, 1994).

Further, determining a withdrawal time of an immunosuppressive agent is generally difficult. For example, tissue engraftment may be achieved without continued administration of an immunosuppressive agent. In that case, casually continued administration of an immunosuppressive agent may cause damage to a patient simply due to toxicity.

On the other hand, discontinued administration of an immunosuppressive agent may cause successfully engrafted tissue to start showing rejection. In this case, restarted administration of an immunosuppressive agent is often not effective to suppress rejection.

Meanwhile, various studies of organ transplantation have been conducted. For example, successful engraftment of a transplant without administering an immunosuppressive agent has been reported in a rat orthotopic liver transplantation (OLT) system, when donor DA rat liver (MHC haplotype RT1a) having a high transplant engraftment rate is transplanted to a recipient PVG rat (RT1c) (Nonpatent Literature 2: Transplantation, 35, 304-311-1983).

Further, there is a report that transplant rejection is suppressed by a single preoperative administration of blood serum of a recipient PVG rat having DA rat liver transplanted (post-OLT serum) to a transplant model system in a combination where rejection occurs (Nonpatent Literature 3: J. Surg. Res., 80, 58-61, 1998).

Further, disclosed is that rejection is suppressed and a recipient is survived by postoperative administration of anti-histone H1 polyclonal antibody to a cardiac transplant system (inch vivo) of a DA (RT1a) and LWIS rat (RT1L) in which rejection certainly occurs (Nonpatent Literature 4: Transplantation, 77, 1595-1603, 2004).

Furthermore, some of the present inventors have disclosed that mixed lymphocyte culture reaction (MLR) is suppressed by using post-transplant initial blood serum from PVG rat, and the anti histone H1 antibody shows MLR suppressive activity (Patent Literature 1: Japanese Patent Laid-Open No. 2004-149507).

Moreover, some of the present inventors have disclosed that anti histone H1 monoclonal antibody is produced, and the anti histone H1 monoclonal antibody produced by hybridoma 16G9 (Deposition Number FERM BP-10413) binds to a peptide consisting of an amino acid sequence represented by SEQ ID NO: 1 obtained by the phage display method (Patent Literature 2: WO2006/025580).

Even further, some of the present inventors have reported that a polyclonal antibody is produced, an antigen of which is a peptide consisting of an amino acid sequence represented by SEQ ID NO: 1 (Patent Literature 3: US-2009-0081247-A1).

However, creating a monoclonal antibody having excellent immunosuppressive activity which can be used to suppress transplant rejection in organ transplantation is still needed.

CITATION LIST

Nonpatent Literature

Nonpatent Literature 1: Transplantation, 58, 170-178, 1994

Nonpatent Literature 2: Transplantation, 35, 304-311, 1983

Nonpatent Literature 3: J. Surg. Res., 80, 58-61, 1998

Nonpatent Literature 4: Transplantation, 77, 1595-1603, 2004

Patent Literature

Patent Literature 1: Japanese Patent Laid-Open No. 2004-149507

Patent Literature 2: WO2006/025580

Patent Literature 3: US-2009-0081247-A1

SUMMARY OF INVENTION

The present inventors have found a novel monoclonal antibody having excellent immunosuppressive activity and an antigen binding fragment thereof, and a hybridoma producing them. The present invention is based on these findings.

Therefore, an object of the present invention is to provide a novel monoclonal antibody having excellent immunosuppressive activity and an antigen binding fragment thereof, and a hybridoma producing them.

Accordingly, the monoclonal antibody of the present invention or an antigen binding fragment binds to a peptide comprising an amino acid sequence represented by SSV-LYGGPPSAA (SEQ ID NO: 1) or a conjugate of this peptide and a pharmaceutically acceptable carrier, and the monoclonal antibody of the present invention or an antigen binding fragment has a higher binding affinity for core histone than for histone H1.

Further, the hybridoma of the present invention produces the above-mentioned monoclonal antibody or an antigen binding fragment.

The monoclonal antibody of the present invention has significant immunosuppressive activity and can be advantageously used to suppress transplant rejection in organ transplantation.

DESCRIPTION OF EMBODIMENTS

Deposition

Figure 1:
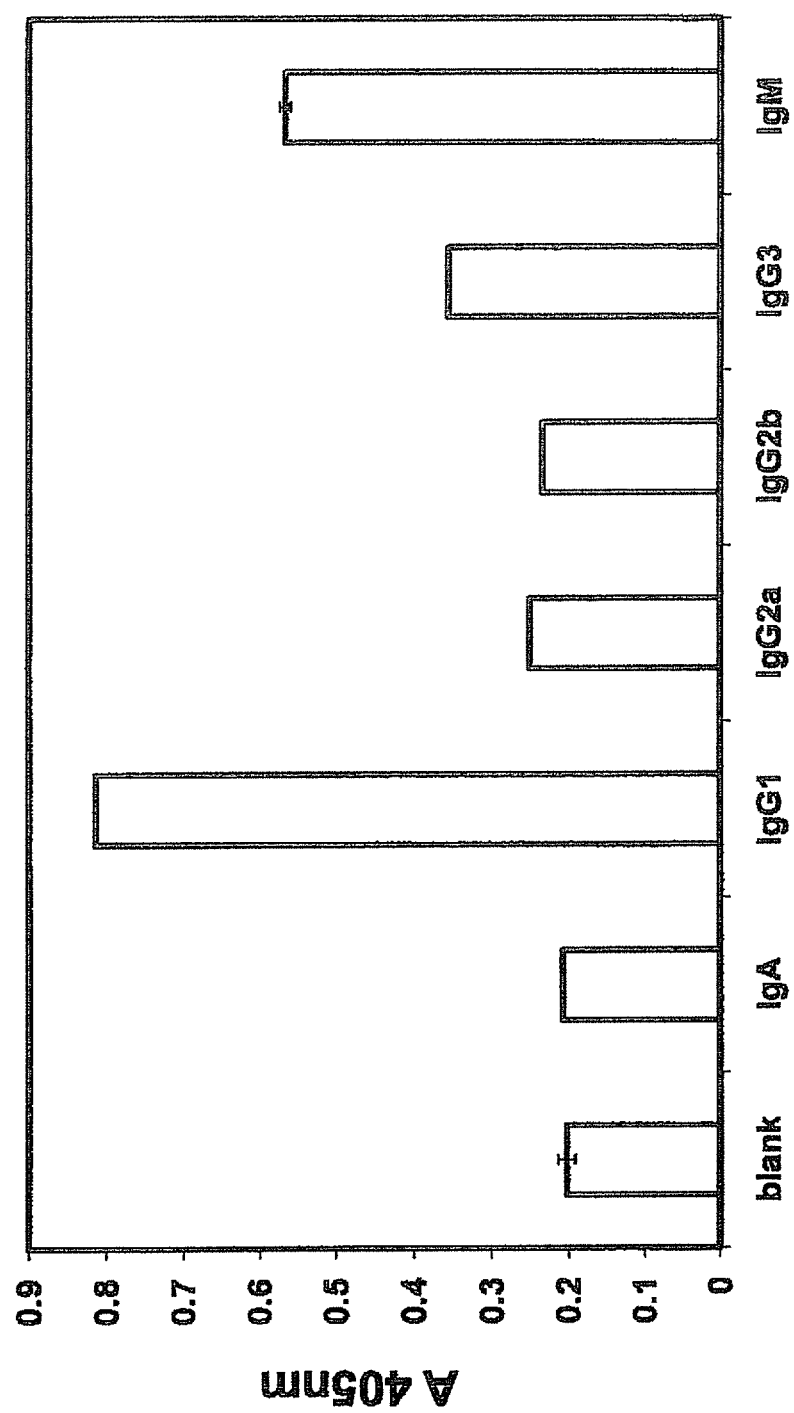
FIG. 1 shows the results from the tests for identifying the isotype of the monoclonal antibody of the present invention (hereinafter, also referred to as "SSVmAb").

The hybridoma of the present invention Mouse-Mouse hybridoma SSV-C 93-3 was deposited at National Institute of Technology and Evaluation, Patent Microorganisms Depositary (Address: Biotechnology Headquarter, 2-5-8 Kazusa Kamatari, Kisarazu-shi, Chiba-ken, Japan) on the original deposition day of Aug. 17, 2010 under the deposition-number NITE BP-972.

Monoclonal Antibody and Hybridoma

One characteristics of the monoclonal antibody of the present invention or an antigen binding fragment thereof is that the monoclonal antibody of the present invention or an antigen binding fragment thereof binds to a peptide consisting of an amino acid sequence represented by SSVLYGGPPSAA (SEQ ID NO: 1) or a conjugate of the peptide and a pharmaceutically acceptable carrier, and that the monoclonal antibody of the present invention or an antigen binding fragment thereof has higher binding affinity for core histone than for linker histone (histone H1). Surprisingly, the present inventors have found that the monoclonal antibody having such reactivity or an antigen binding fragment thereof has significant immunosuppressive activity.

According to a preferred aspect of the present invention, the above-mentioned antibody or an antigen binding fragment thereof is against a peptide consisting of an amino acid sequence represented by SSVLYGGPPSAA (SEQ ID NO: 1) or, the peptide and a pharmaceutically acceptable carrier.

According to another preferred aspect of the present invention, core histone is histone H2A, H2B, H3 or H4, and more preferably H2A, H3 or H4.

The antibody of the present invention or an antibody binding fragment thereof may also comprise a heavy chain and/or a light chain. Each of a light chain and a heavy chain may have a variable region at its N-terminal, and each variable region may contain four framework regions (FR) and three complementarity determining regions (CDR) in an alternate fashion. Conventionally, residues in a variable region are numbered according to the system devised by Kabat et al. The system is described in Kabat et al., 1987, Sequences of Proteins of Immunological Interest, US Department of Health and Human Services, NIH, USA. Unless otherwise stated, this numbering system is used in the present specification. Numbering based on the method by Kabat et al. can be easily performed, for example, using the web site at http://www.bioinf.org.uk/abysis/tools/analyze.cgi.

The Kabat nomenclature of residues does not necessarily correspond to the linear numbering of amino acid residues directly. An actual linear amino acid sequence in either a structural element of the basic structure of a variable region, a framework or a CDR may have a fewer or additional amino acid compared with the strict Kabat numbering depending on its trancation or insertion. For a given antibody, correct Kabat numbering of residues will be determined by aligning homologous residues in a sequence numbered according to the "standard" Kabat numbering and in a sequence of the antibody.

According to one aspect, the light chain variable region of the antibody of the present invention or an antigen binding fragment thereof comprises CDR1 consisting of an amino acid sequence represented by RASSSVSYMH (SEQ ID NO: 2), CDR2 consisting of an amino acid sequence represented by ATSNLAS (SEQ ID NO: 3) and CDR3 consisting of an amino acid sequence represented by QQWSSNPWT (SEQ ID NO: 4). According to a more preferred aspect, the above-mentioned light chain variable region comprises an amino acid sequence represented by Position 23 to Position 128 of SEQ ID NO: 6.

According to another aspect, the heavy chain variable region of the antibody of the present invention or an antigen binding fragment thereof comprises CDR1 consisting of an amino acid sequence represented by GYNMN (SEQ ID NO: 7), CDR2 consisting of an amino acid sequence represented by NINPYYGSTSYNQKFKG (SEQ ID NO: 8) and CDR3 consisting of an amino acid sequence represented by SPYYSNYWRYFDY (SEQ ID NO: 9). According to a more preferred aspect, the above-mentioned heavy chain variable region comprises an amino acid sequence represented by Position 20 to Position 141 of SEQ ID NO: 11.

Further, according to an even more preferred aspect of the present invention, the antibody of the present invention or an antigen binding fragment thereof comprises a light chain variable region comprising CDR1 consisting of an amino acid sequence represented by RASSSVSYMH (SEQ ID NO: 2), CDR2 consisting of an amino acid sequence represented by ATSNLAS (SEQ ID NO: 3) and CDR3 consisting of an amino acid sequence represented by QQWSSNPWT (SEQ ID NO: 4), and a heavy chain variable region comprising a heavy chain variable region comprising CDR1 consisting of an amino acid sequence represented by GYNMN (SEQ ID NO: 7), CDR2 consisting of an amino acid sequence represented by NINPYYGSTSYNQKFKG (SEQ ID NO: 8) and CDR3 consisting of an amino acid sequence represented by SPYYSNYWRYFDY (SEQ ID NO: 9).

Furthermore, according to an even more preferred aspect of the present invention, the antibody of the present invention or antigen binding fragment thereof comprises a light chain variable region comprising an amino acid sequence represented by Position 23 to Position 128 of SEQ ID NO: 6 and a heavy chain variable region comprising an amino acid sequence represented by Position 20 to Position 141 of SEQ ID NO: 11.

Moreover, according to a preferred aspect of the present invention, the above-mentioned monoclonal antibody or an antigen binding fragment thereof can downregulate the activity of ATP synthase. In addition, according to a more preferred aspect of the present invention, the above-mentioned ATP synthase is mitochondria ATP synthase.

The above-mentioned binding affinity and the downregulation activity of ATP synthase activity of the monoclonal antibody of the present invention or an antigen binding fragment thereof are determined, for example, by the methods described in Test Examples 2 and 4 of the present specification.

Further, the monoclonal antibody of the present invention is preferably a chimeric antibody, a humanized antibody or a fully human antibody. Those skilled in the art can produce these antibodies according to known technologies in the art as described in, for example, Morrison, S.L., Oi, V. T., "immunoglobulin genes" Academic Press (London), 260-274 (1989); Roguska, M. L. et. Al., Humanization of murine monoclonal antibodies through variable domain resurfacing, Proc. Natl. Acad. Sci. USA, 91, 969-973 (1994); Tomizuka, K. et. al. Functional expression and germline transmission of a human chromosome fragment in chimaeric mice, Nature Genet., 16, 133-143 (1997); Winter, G. et. al., Making antibodies by phage display technology, Ann. Rev. Immunol., 12, 433-455 (1994); Griffiths, A. D. et. al., Isolation of high affinity human antibodies directly from large synthetic repertoires, EMBO. J., 13, 3245-3260 (1994).

Furthermore, according to a preferred aspect of the present invention, the above-mentioned antigen binding fragment is preferably Fab, Fab', (Fab')$_2$, Fv or scFv.

Moreover, according to another aspect of the present invention, provided is a hybridoma which produces the above-mentioned monoclonal antibody or an antigen binding fragment thereof. In addition, according to another preferred aspect of the present invention, the hybridoma is Mouse-Mouse hybridoma SSV-C 93-3.

The monoclonal antibody of the present invention or an antigen binding fragment thereof, and a hybridoma can be produced, for example, as follows. That is, first, the hybridoma of the present invention can be obtained using a peptide comprising an amino acid sequence represented by SSVLYGGPPSAA (SEQ ID NO: 1) or a conjugate of this peptide and a pharmaceutically acceptable carrier as an antigen by fusing mammalian plasma cells (immune cells) immunized by this sensitizing antigen with mammalian myeloma cells, and cloning and screening the resulting hybridomas. Then the monoclonal antibody of the present invention can be obtained by culturing the hybridoma of the present invention and collecting antibody produced by it.

For methods of immunizing a mammal, any common administration methods in the art can be used. In particular, they include intraperitoneal injection, intrasplenic injection, intramuscular injection, subcutaneous injection, intradermal injection, oral administration, transmucosal administration, transdermal administration, but preferably they are intraperitoneal injection, intrasplenic injection. The dosage interval of a sensitizing antigen is appropriately determined depending on a dose of the sensitizing antigen, a species of the mammal and the like. For example, it can be several times per month.

Mammals to be immunized are not particularly limited, but preferably selected after considering, for example, compatibility with myeloma cells used for cell fusion. They include, for example, mouse, rat and hamster. Preferably, the mammal is mouse.

Further, splenic cells are preferably used as immune cells.

Myeloma cells used for the present invention include, for example, P3 (P3X63Ag8.653) (J. Immunol., 123, 1548, 1978), p3-U1 (Current Topics in Micro-biology and Immunology, 81, 1-7, 1978), NS-1 (Eur. Immunol., 6, 511-519, 1976), MPC-11 (Cell, 8, 405-415, 1976), Sp2/0-Ag14 (Nature, 276, 269-270, 1978), FO (J. Immunol. Meth., 35, 1-21, 1980), S194 (J. Exp. Med., 148, 313-323, 1978) and R210 (Nature, 277, 131-133, 1979). The myeloma cell is preferably P3 or p3-U1, more preferably P3.

Immune cells and myeloma cells can be fused, for example, by a method according to Milstein et. al. (Methods Enzymol., 73, 3-46, 1981). Specifically, cell fusion can be performed, for example, by mixing immune cells and myeloma cells in culture medium in the presence of a fusion promoter. Then, additon of culture medium and centrifugation can be appropriately repeated during cell fusion to produce hybridomas.

Culture media used for cell fusion include, for example, culture media usually used in cell fusion such as RPMI-1640 culture medium and MEM culture medium. Further, blood serum supplements such as fetal calf serum (FBS) can be suitably used together.

Temperature for cell fusion is preferably 25 to 37° C., and more preferably 30 to 37° C.

A mixing ratio of myeloma cells and immune cells is preferably about 1:1 to 1:10.

Fusion promoters may include, for example, polyethylene glycol (PEG) and Sendai Virus (HVJ). The fusion promoter is preferably PEG. The molecular weight of PEG can be suitably selected, and for example, the average molecular weight can be between about 1,000 and 6,000. The concentration of PEG in culture medium is preferably about 30 to 60% (W/V).

Auxiliary agents such as dimethyl sulfoxide can be suitably added to culture medium as desired.

Selection of the hybridoma of the present invention can be performed by culturing hybridomas obtained by cell fusion, for example, in common selection medium such as HAT culture medium, and using the limiting dilution method to conduct screening for, for example, on the basis of an indicator such as an antibody titer against a peptide consisting of an amino acid sequence represented by SSVLYGGPPSAA (SEQ ID NO: 1) or a conjugate of the peptide and a pharmaceutically acceptable carrier. A culture period in HAT culture medium is a sufficient period for cells (non fused cells) other than the hybridoma of interest to die, and usually can be several days to several weeks. The hybridoma of the present invention obtained in this way can be sub-cultured in common culture medium, and also can be stored for a long time in liquid nitrogen.

Methods of harvesting the monoclonal antibody of the present invention or an antibody binding fragment thereof include, for example, a method where hybridoma is cultured according to the conventional method to obtain monoclonal antibody and the like from the culture supernatant or a method where hybridoma is administered to a compatible mammal for proliferation and monoclonal antibody and the like is obtained from its ascitic fluid. Here, the former method is preferred for obtaining highly pure antibody while the latter method is preferred for producing a large amount of antibody.

Further, the monoclonal antibody of the present invention or an antibody binding fragment thereof can be purified to a high purity by methods such as salting-out, gel filtration and affinity chromatography.

The monoclonal antibody of the present invention or an antigen binding fragment thereof has significant immunosuppressive activity as described above. The monoclonal antibody of the present invention or an antigen binding fragment thereof may be used as it is, or may be used as a pharmaceutical composition along with a pharmacologically acceptable additive. Therefore, according to one aspect of the present invention, provided is a pharmaceutical composition comprising the monoclonal antibody of the present invention or an antigen binding fragment thereof. Further, according to a preferred aspect of the present invention, the above-mentioned pharmaceutical composition is used as an immunosuppressive agent. Furthermore, according to another aspect of the present invention, provided is the use of the monoclonal antibody of the present invention in manufacturing a pharmaceutical composition.

The pharmaceutical composition of the present invention can be advantageously used to suppress rejection of transplanted organs such as heart, kidney, liver, bone marrow and skin or to reduce risk of developing rejection, and further used to treat autoimmune diseases and the like. The pharmaceutical composition of the present invention can be prepared, for example, by desolving the monoclonal antibody of the present invention in injectable saline, injectable distilled water, an injectable buffer solution and the like. The composition for immunosuppression of the present invention may further contain a suitable solvent, a solubilizing agent, a preserving agent, a stabilizing agent, an emulsifying agent, a suspending agent, a soothing agent, a tonicity adjusting agent, a buffer, an excipient, a thickener, a coloring agent, a known carrier (various liposomes, polyamino acid carriers, synthetic macromolecules, naturally-occurring polymers and the like) and the like.

Further, according to another aspect of the present invention, provided is a method of treating a mammal in need of immunosuppression, the method comprising: administrating an effective amount of the monoclonal antibody of the present invention or an antigen binding fragment there. In this context, the term "treating" means alleviating established pathology. Furthermore, according to another aspect of the present invention, provided is a method of reducing risk of developing transplant rejection, the method comprising: administering an effective amount of the monoclonal antibody of the present invention or an antigen binding fragment thereof to a mammal which has received organ transplantation.

Moreover, according to one aspect, the above-mentioned mammal has received organ transplantation. The above-mentioned mammals and donors for organ transplantation include human, swine and baboon. They are preferably human.

Organs to be transplanted include, for example, liver, heart, kidney and skin.

Further, the monoclonal antibody of the present invention or an antigen binding fragment thereof may be simultaneously or sequentially administered to a mammal in combination with other immunosuppressive agents used for organ transplantation. Such other immunosuppressive agents include, but not limited to, for example, alkylating agents, such as cyclophosphamide; antimetabolites such as azathioprine, methotrexate and mizoribine; inhibitors for T-cell activity such as ciclosporin and tacrolimus; steroids such as prednisolone, methylprednisolone, mycophenolate mofetil and azathioprine; inhibitors for lymphocyte surface functional such as basiliximab and muromonab; and combinations thereof.

Further, the monoclonal antibody of the present invention or an antigen binding fragment thereof can be administered systemically or locally. Specific methods of administration include infusion, intravenous injection, intramuscular injection, subcutaneous injection, intradermal injection, oral administration, transmucosal administration and transdermal administration.

Furthermore, the effective amount of the monoclonal antibody of the present invention or an antigen binding fragment is not particularly limited, and can be suitably determined by the person skilled in the art depending on species, nature, sex, age and the like of the mammal. For example, such effective amounts include one or several doses of 0.05 to 40 mg/kg weight/day, preferably 0.1 to 1.0 mg/kg weight/day.

EXAMPLES

In the followings, the present invention will be specifically described with reference to Examples, but the present invention is not limited to these Examples.

Example 1

Production of Monoclonal Antibody (SSVmAb)

Production of an Antigenic Substance

For an antigenic substance, a conjugate of a peptide consisting of an amino acid sequence represented by SEQ ID NO: 1 and KLH were used.

In preparation of the antigenic substance, first, a peptide consisting of an amino acid sequence represented by SEQ ID NO: 1 was synthesized by the Fmoc peptide solid phase synthesis method (a manufacturing instrument; Applied Biosystems ABI 430). A conjugate of the above-mentioned peptide and KLH (SIGMA) was synthesized by stirring 5 mg of the above-mentioned peptide, about 20 mg KLH and 30 µg glutaraldehyde (Katayama Chemical Industries Co., Ltd.) in phosphate buffer (pH 8.0) at room temperature for about 6 hours.

Production of Hybridoma

Immunization

Suspension (the concentration of the antigen: 0.25 mg/mL) was obtained by mixing 0.8 mL of a solution in which the antigenic substance was dissolved in PBS (the concentration of the antigenic substance: 0.5 mg/mL) and 0.8 mL complete Freund's adjuvant (Wako Pure Chemical Industries, Ltd.). Then, 0.2 mL of this suspension was intraperitoneally administered to a BALB/c mouse. This suspension in the same amount was further administered to the mouse every two weeks. Then, 16 weeks after the administration was started, 0.2 mL of a solution in which the antigen was dissolved in PBS (the concentration of the antigen: 600 to 1000 mg/mL) was intraperitoneally administered to the mouse as a final dose. Note that blood was withdrawn via a vein at the back of the eye when administering, and an antibody titer was measured by ELISA. Four days after the last administration, exsanguination was performed, and the blood obtained was centrifuged (2000 rpm, 20 minutes) to obtain antiserum, which was used as control antiserum in the following experiments. Further, after exsanguination, splenic cells was removed from the rat, and the splenic cells obtained were used in cell fusion as follows.

Cell Fusion

The above-mentioned splenic cells and myeloma cells (P3×63-Ag.8.653) were mixed at splenic cells:myeloma cells=10:1 to 10, and centrifuged (1500 rpm, 5 minutes). After centrifugation, the supernatant was removed by using an aspirator, and 1 mL polyethylene glycol 4000 (50% PBS solution) at 37° C. was added over 1 minute to the cell pellet obtained to form a mixed liquid. After allowing this mixed liquid to stand at 37° C. for 1 minute, 1 mL IMDM culture medium at 37° C. was each added every 30 seconds (total 9 mL), and then centrifuged (1500 rpm, 5 minutes). After centrifugation, the supernatant was removed by suction, and an appropriate amount of 15% FCS (JRH BIOSCIENCES) containing IMDM (GIBCO) culture media at 37° C. was added. The suspension obtained was dispensed into a 96 well culture plate in an amount of 100 mL for each, and cultured for one day in an incubator at 37° C./5% $CO_2$. Further, 100 mL HAT culture medium (HAT powder (HAT MEDIA SUPPLEMENT (×50), SIGMA) was dissolved in 10 mL serum free IMDM culture medium, which was then diluted 50 times with 10% FCS containing IMDM culture medium) was added, and cultured in an incubator at 37° C./5% $CO_2$. HAT culture medium was replaced every 2 to 3 days, and after 10 days, it was switched to HT culture medium (HT powder (HT MEDIA SUPPLEMENT, SIGMA) was dissolved in 10 mL serum free IMDM culture medium, which was then diluted 50 times with 10% FCS containing IMDM culture medium.), and cultured in an incubator at 37° C./5% $CO_2$ for three days. After that, the culture medium (HT culture medium) was replaced every 2 to 3 days. After verifying cell growth under a microscope, the culture supernatants (about 100 mL) were collected. Using the culture supernatants, screening of hybridoma was performed by measuring antibody titers.

Screening of Hybridoma Cells
Measurement of Antibody Titer

A buffer solution containing the above-mentioned antigenic substance (5 mg) (Baicarbonate buffer: 100 mM $NaHCO_3$—NaOH, pH 9.2 to 9.5, the concentration of the peptide: 1 μg/mL) was added to a 96 well flat bottom plate in an amount of 50 μL per well, and allowed to stand for coating at room temperature for 2 hours. The plate was washed 3 times with wash buffer (PBST), and then blocking buffer (3% skim milk 1% BSA, PBS) was added in an amount of 200 to 250 μL/well to react at 4° C. for one full day, and then washed 3 times. Then the culture supernatant of hybridoma was added in an amount of 100 μL/well, which was allowed to react at 37° C. for 4 hours or at 4° C. for one full day. After the plate was washed 3 times, biotin-labeled anti-mouse IgG (SIGMA) diluted 10000 times with dilution buffer (10 mM Tris-HCl (pH 8.0), 0.9% (W/V) NaCl, 0.05% (W/V) Tween 20) was added in an amount of 50 μL/well, which was allowed to react at room temperature for 2 hours. After washing was performed 6 times, alkaline phosphatase labeled Streptaridin diluted 1000 times with dilution buffer was added in an amount of 50 μL/well, which was allowed to react at room temperature for 1 to 2 hours. Then washing was performed 6 times, and fluorescent substrate buffer (Attophos substrate buffer, Roche Diagnostics K.K.) was added in an amount of 50 μL/well, and the plate was shaded to allow fluorescence to develop. Fluorescence intensity was measured in CytoFluorII (PerSeptive Biosystems).

Screening of Hybridoma

To the wells which showed a positive result in the above-mentioned measurement of antibody titer ($1 \times 10^5$ cells/mL), 15% FCS 10% HCF (Hybridoma cloning factor, ORIGIN) containing IMDM culture medium was added, which was dispensed in a 96 well culture plate in an amount of about 200 cells/well, and cultured in an incubator at 37° C. 5% $CO_2$. Then antibody titers were measured as described above, hybridomas showing a high antibody yield were selected.

Limiting dilution was further performed so that the selected hybridoma was diluted to 0.5 to 1 cell/well with 15% FCS 10% HCF containing IMDM culture medium. After culturing in an incubator at 37° C./5% $CO_2$ for about three to four days, antibody titers were measured as described above to select hybridomas showing a high antibody yield. Limiting dilution was further repeated to obtain hybridomas which produce monoclonal antibody against the above-mentioned antigenic substance. Among these, the hybridoma with the highest antibody titer was selected and designated as Mouse-Mouse hybridoma SSV-C 93-3.

Acquisition of Monoclonal Antibody

Hybridoma Mouse-Mouse hybridoma SSV-C 93-3 was cultured using 15% FCS containing RPMI culture medium ($1 \times 10^6$ cells/mL). Then, hybridoma culture medium was collected, and filtered through a filter in order to remove dead cell debris. Then, ammonium sulfate was added to the culture supernatant to a final concentration of 40%, and stirred at 40° C. for 1 hour. Then, centrifugation (3000 g, 30 minutes, 4° C.) was performed, and the supernatant was discarded to collecte precipitate. The precipitate was dissolved in a volume of PBS equivalent to a ⅒ amount of the above-mentioned culture supernatant and dialyzed against PBS overnight.

Then, the above-mentioned precipitate was diluted twice with 20 mM sodium phosphate buffer (pH 7.0), and loaded onto a HiTrap NHS activated column along with 1 M Tris-HCl buffer. Then, antibody was eluted with a 0.1 M glycine HCl solution (pH 2.7), and collected in fraction tubes.

Test Example 1

Identification of SSVmAb Isotype

In order to identify the isotype of the monoclonal antibody (SSVmAb) of Example 1, isotype identification tests were performed using Mouos Monoclonal Antibody Isotyping Reagents (SIGMA).

The results are shown in FIG. 1, indicating that IgG1 showed the highest value.

Further, when mouse IgG1 (eBioscience) and the monoclonal antibody (SSVmAb) of Example 1 were reduced by 2-mercaptoethanol and analyzed by SDS-PAGE, the bands corresponding to a heavy chain and a light chain were observed at similar positions (50 KD, 25 KD) for both. On the other hand, similar bands were not observed, when a similar experiment was conducted using mouse IgM (eBioscience) instead of mouse IgG1.

From FIG. 1 and the results of SDS-PAGE, the isotype of the monoclonal antibody (SSVmAb) of Example 1 was determined to be IgG1.

Test Example 2

Determination of the Affinity of SSVmAb for Core Histone

WO2006/025580 has reported the monoclonal antibody (16G9 mAb) produced by hybridoma 16G9 (Deposition Number FERM BP-10413) as an anti H1 monoclonal antibody which can be used for immunosuppression and which binds to a peptide consisting of an amino acid sequence represented by SEQ ID NO: 1.

Therefore, using the antibody (16G9 mAb) described in WO2006/025580 as a Reference Example 1, the affinity for an antigen was compared with that of the monoclonal antibody (SSVmAb) of Example 1.

For an antigen, histone H1, which is an antigen of Reference Example 1 (16G9 mAb), and core histone H2A, H2B, H3 and H4, which are histone H1 antigen analogs, were selected.

The Affinities between histone H1 or core histone and SSVmAb were determined by ELISA.

A 96 well microplate was coated with histone H1, H2A, H2B, H3 or H4. Each histone used was dissolved in 100 mM sodium carbonate buffer (pH 9.3). The plate was washed with PBS-tween 20 (0.05%), and blocked with 3% skim milk and 1% BSA for 1 hour. To each well, 5 µg/mL SSVmAb was added, and incubated for 1 hour. Bound SSVmAb was detected using peroxidase (HRP) conjugated anti mouse IgG1Ab (SIGMA), and incubated for 1 hour. Bound SSVmAb was detected using the ABTS [2,2'-azino-bis(3-ethylbenzothiazoline-sulfonic acid)] substrate solution, and absorbance at 405 nm was measured using Multiskan Ascent (Thermo Fisher Scientific Inc., Waltham, Mass.).

Figure 2:
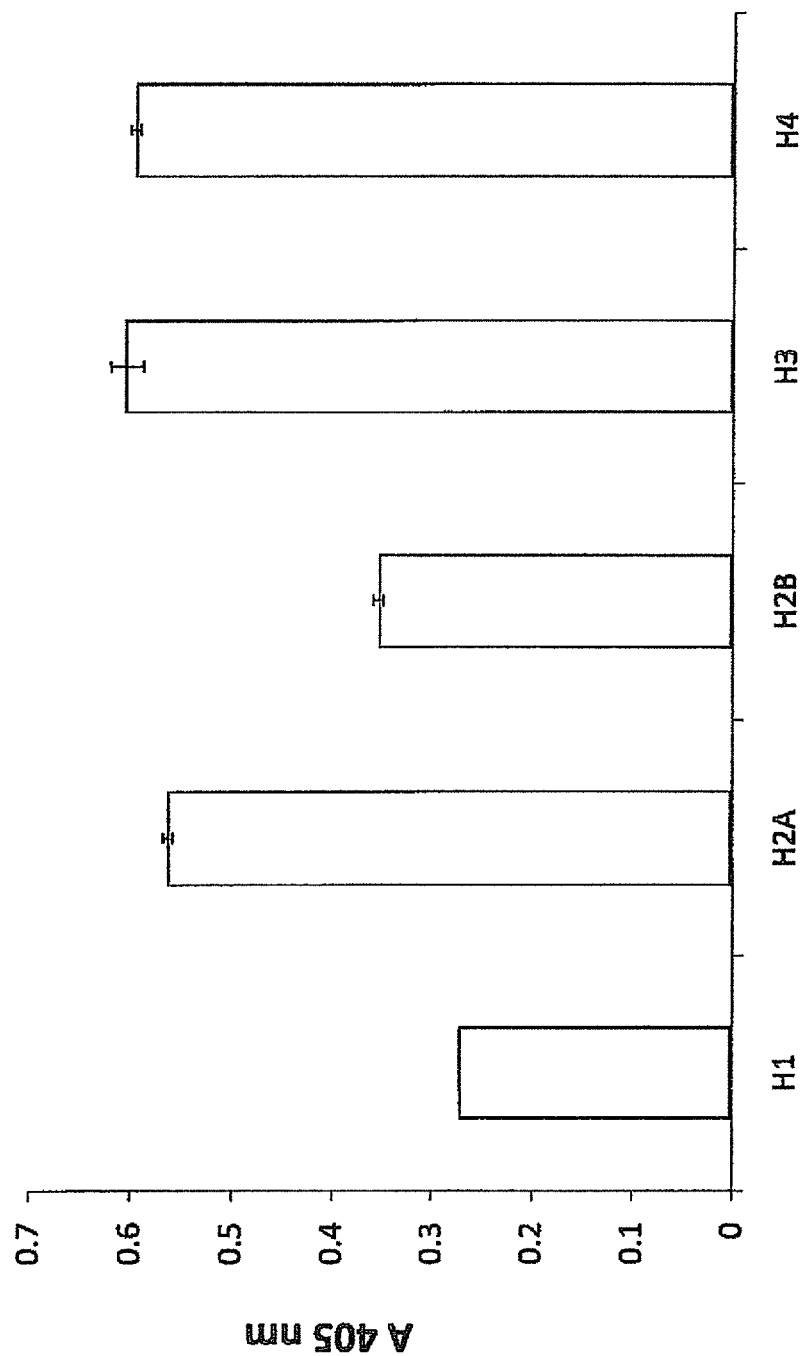
FIG. 2 shows the results from the tests in which the binding affinities of the monoclonal antibody of the present invention (SSVmAb) for histone H1, histone H2A, H2B, H3 or H4 were compared.
Figure 3:
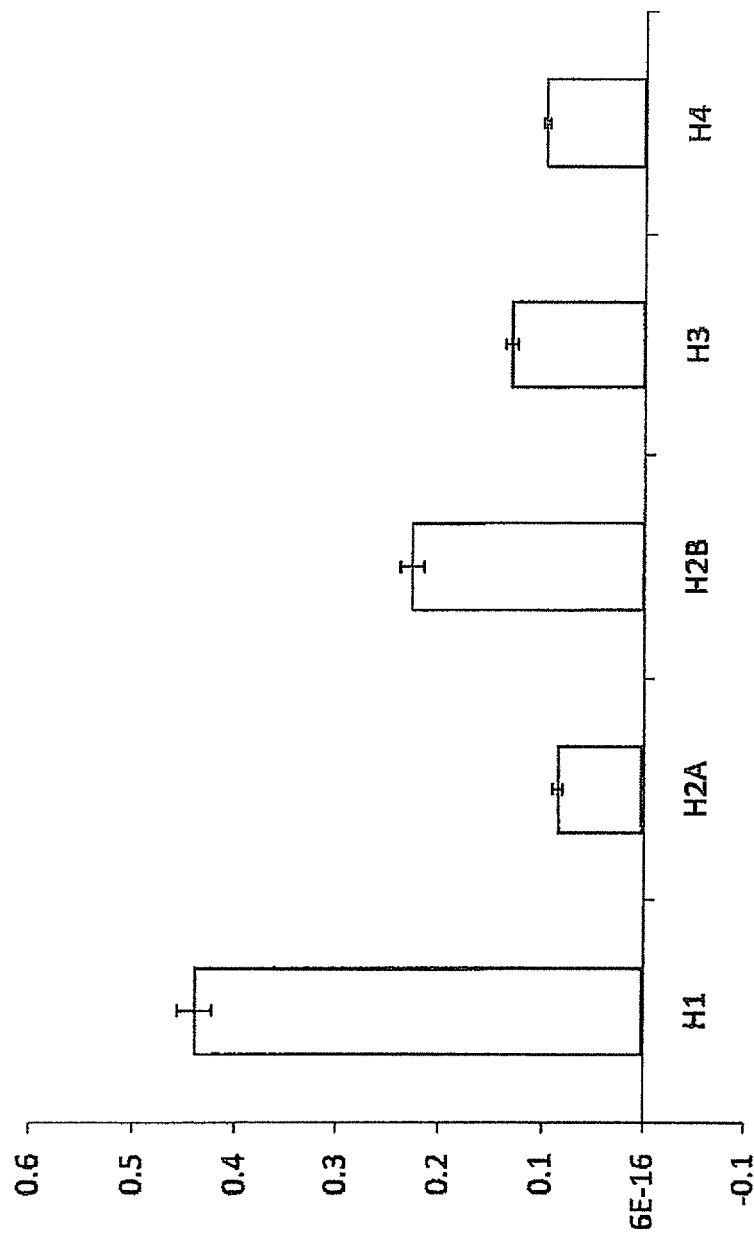
FIG. 3 shows the results from the tests in which the binding affinities of the monoclonal antibody produced by hybridoma 16G9 (hereinafter, also referred to as "16G9 mAb") for histone H1, histone H2A, H2B, H3 or H4 were compared. The hybridoma has been deposited under the deposition number FERM BP-10413 (Reference).

The results are shown in FIGS. 2 and 3.

As shown in FIG. 2, for Example 1 (SSVmAb), the affinities for histone H2A, H2B, H3 or H4 were higher than the affinity for histone H1.

On the other hand, as shown in FIG. 3, for Reference Example 1 (16G9), the affinity for histone H1 was higher than the affinities for histone H2A, H2B, H3 and H4.

Test Example 3

MLR Tests

Spleen lymphocytes from a naive DA rat (responsive cells) and spleen lymphocytes from a LEW rat treated with mitomycin-C (Kyowa Hakko Kogyo Co., Ltd.) were used. The responsive cells were adjusted to $5\times10^5$ cells/mL with 10% FCS—RPMI culture medium, and the stimulated cells were adjusted to $8\times10^6$ cells/mL with 10% FCS—RPMI culture medium. After plating the responsive cell suspension and the stimulated cell suspension in an amount of 100 µL to a 96 well round-bottom plate (Nunc Brand Products) respectively, the monoclonal antibody 16G9 mAb of Reference Example 1 (0.1, 2, 4, or 6 µg/mL/well) or the monoclonal antibody SSVmAb of Example 1 (4 µg/mL/well) was added at the start of mixed culture, and cultured for 3.5 days or longer under the conditions of 37° C., 5% $CO_2$/95% air. In addition, an immunosuppressive agent tacrolimus (FK506: Fujisawa Pharmaceutical Co., Ltd., 1 nM/well) was added as a positive control. Further, 10 µL bromo deoxyuridine (BrdU) was added 15 hours before the end of culture. Then the proliferation potential of the cells treated with the immunosuppressive agent was measured using BrdU labeling & detection kit III (Roche Diagnostics K.K.) using the amount of BrdU incorporated into cellular DNA as an indicator. The proliferation potential was used as an indicator for a level of immunosuppression.

Figure 4:
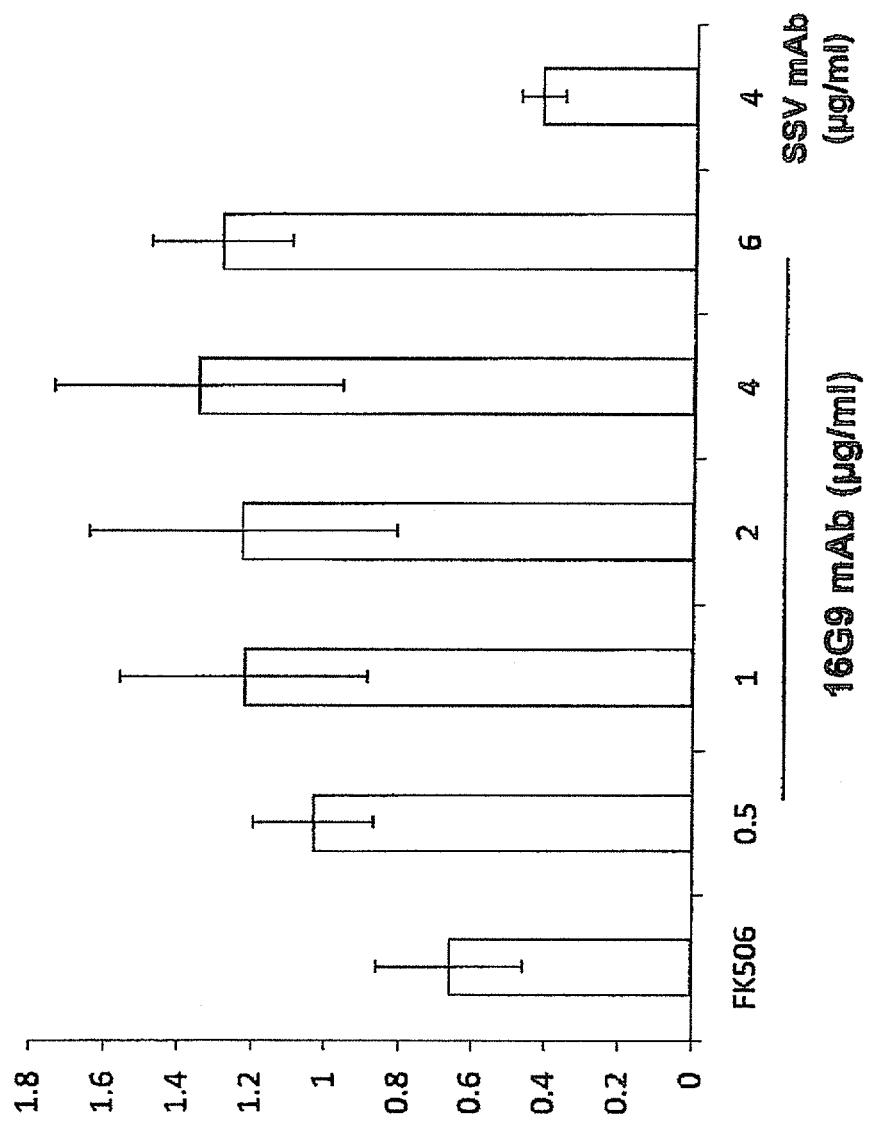
FIG. 4 shows the results from the tests for mixed lymphocyte reaction (MLR) using the monoclonal antibody of the present invention (SSVmAb) and 16G9 mAb.

The results are shown in FIG. 4.

For Example 1 (SSVmAb), the absorbance which indicates the amount of incorporated BrdU was lower than that of Reference Example 1 (16G9 mAb) and tacrolimus (FK506). In particular, when the absorbance 0.552±0.114 (mean±S.E.) of Example 1 (SSV mAb) and the absorbance 1.351±0.389 (mean±S.E.) of Reference Example 1 (16G9 mAb) where the same amount was added (4 µg/mL/well) were compared, the mean of Example 1 was about 41% of that of Reference Example 1.

Test Example 4

Determination of the Reactivity of the Monoclonal Antibody (SSVmAb) with T Cells Using the following approach, spleen was removed from a C57BL/6 mouse (5 weeks old, female, CHARLES RIVER LABORATORIES JAPAN, INC.) to prepare whole splenic cells.

First, in a 5 ml culture dish (BD Bioscience FALCON 351007) into which 5 ml RPMI 1640 culture medium (Sigma-Aldrich, R-8758) was transferred, spleen was disentangled well with scissors for dissection and forceps to suspend the splenic cells, which were then transferred to a 15 ml centrifuge tube (BD Bioscience FALCON 352096). Then, the 5 ml dish was washed several times with phosphate-buffered saline (PBS, Invitrogen, 20012-027), and these were also added to the foregoing cell suspension and allowed to stand, and then the supernatant was collected in another 15 ml centrifuge tube. In addition, 5 ml RPMI 1640 culture medium was also added to the residual insoluble spleen tissue again and allowed to stand, and then only the supernatant was collected, which was combined with the above-mentioned cell suspension to perform centrifugation at 1,500 rpm for 5 min. To the collected cells, added was 2 ml lysis buffer (150 mM NH4Cl/15 mM $NaHCO_3$/0.1 mM EDTA-$Na_2$, pH 7.3) and hemolyzed by tapping, and then 10 ml PBS was added. After washed 3 times by centrifugation at 1,500 rpm for 5 min, whole splenic cells were obtained.

Next, according to the approach described below, whole T cells were purified from the above splenic cells by magnetic sorting (MACS) using Pan T Cell Isolation Kit, mouse (Miltenyi Biotec, 130-090-861).

First, the splenic cells were suspended at a ratio of $5\times10^7$ cells/200 µl in MACS buffer (0.5% bovine serum albumin (BSA, NACALAI TESQUE, INC., 08777-36)/PBS), to which 50 µl Biotin-antibody cocktail/$5\times10^7$ cells was added and incubated at 4° C. for 10 min. After this was suspended in 150 µl MACS buffer/$5\times10^7$ cells, 100 µl anti-biotin micro beads/$5\times10^7$ cells was added and incubated at 4° C. for 15 min. To this, MACS buffer (10 ml) was added and washed by centrifugation at 1500 rpm for 5 min, and then the recovered cells were suspended in 500 µl MACS buffer. After a MACS column (MS column, Miltenyi Biotec, 130-042-201) was placed in a magnet (MiniMACS separation Unit, Miltenyi Biotec, 130-090-312) and the column was equilibrated with 500 µl MACS buffer, the above-mentioned cell suspension was loaded. The 500 µl flow through fraction and the subsequent column washing fraction (1.5 ml) with MACS buffer were collected to give a purified unstimulated T cells (about 97% pure).

The reactivity of the above unstimulated with 16G9 mAb or SSV mAb was analyzed by flow cytometry (FACS).

First, after each T cell sample ($1\times10^6$ cells) was suspended in 89 µl FACS buffer (0.5% FBS/PBS/0.02% $NaN_3$), 1 µg anti-mouse CD16/32-blocks Fc binding (eBioscience, 14-0161-85) was added and incubated at 4° C. for 20 min. To this, 10 µl 16G9 mAb or SSV mAb (100 µg/ml) was added as a primary antibody and incubated at 4° C. for 60 min. After the cells were washed by centrifugation twice with FACS buffer, a 100 µl volume of a secondary antibody (Biotin-conjugated anti-mouse IgM mAb (eBioscience, 13-5780-85) or Biotin-conjugated rat anti-mouse IgG1mAb (BD Biosciences, 553441), 1 µg/ml each) was added and incubated at 4° C. for 30 min. After the cells were again washed by centrifugation twice with FACS buffer, 100 µl Streptavidin-PE-Cy7 (BD Biosciences, 556463, 1 µg/ml) was added, to which FITC-conjugated rat anti-mouse CD3 mAb (BDBiosciences, 553062) was added to a final concentration of 1 µg/ml and incubated ar 4° C. for 30 min. After washed by centrifugation twice with FACS buffer and filter-treated with a 40 µm cell strainer (BD Bioscience, FALCON 352340), each sample was subjected to a FACSCalibur flow cytometer and CellQuest software (BD Bioscience) to analyze the number of 16G9 mAb or SSV mAb positive/CD3 positive T cells.

Figure 5:
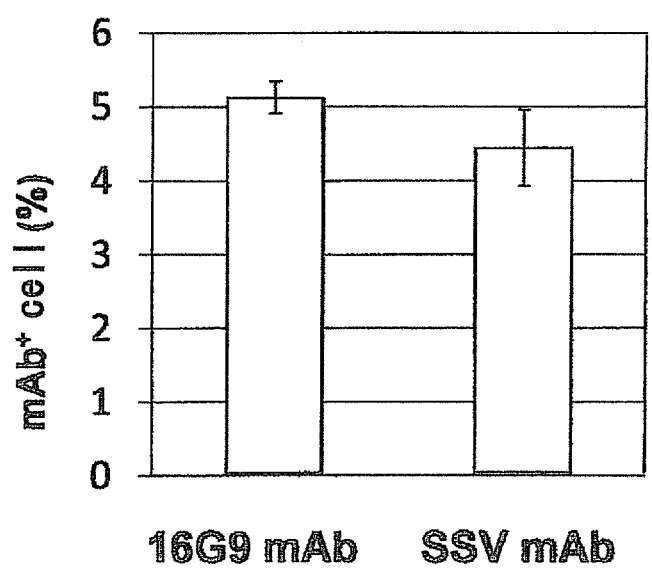
FIG. 5 shows the results from the comparison in which the reactivities of the monoclonal antibody of the present invention (SSVmAb) and 16G9 mAb with T cells were compared by flow cytometry.

The results are shown in FIG. 5.

When Reference Example 1 (16G9 mAb) was compared with Example 1 (SSV mAb), no significant difference was observed for the reactivity with CD3 positive T cells, and these antibodies showed comparative reactivity (student t-test, $p<0.05$).

Test Example 5

Identification of a Target for Down Regulation by SSV mAb

Seven candidate proteins which may be down regulated by Example 1 (SSV mAb) were identified by the proteome analysis.

Then among the 7 candidate proteins, ATP synthase was determined to be a target antigen of Example 1 (SSV mAb) by the method described below.

First, T cells from a Balb/c mouse having mitochondria ATP synthase knocked down were obtained using Accell siRNA kit from Thermo Fisher Scientific Inc.

Next, according to the method in Test Example 2, MLR tests were performed using Example 1 (SSV mAb) as a test substance using the T cells obtained.

In the test, Isotype IgG1 (eBioscience) was used as a control reagent. In addition, a similar test was performed using T cells from a mouse not having the ATP synthase knocked down as a control test.

Figure 6:
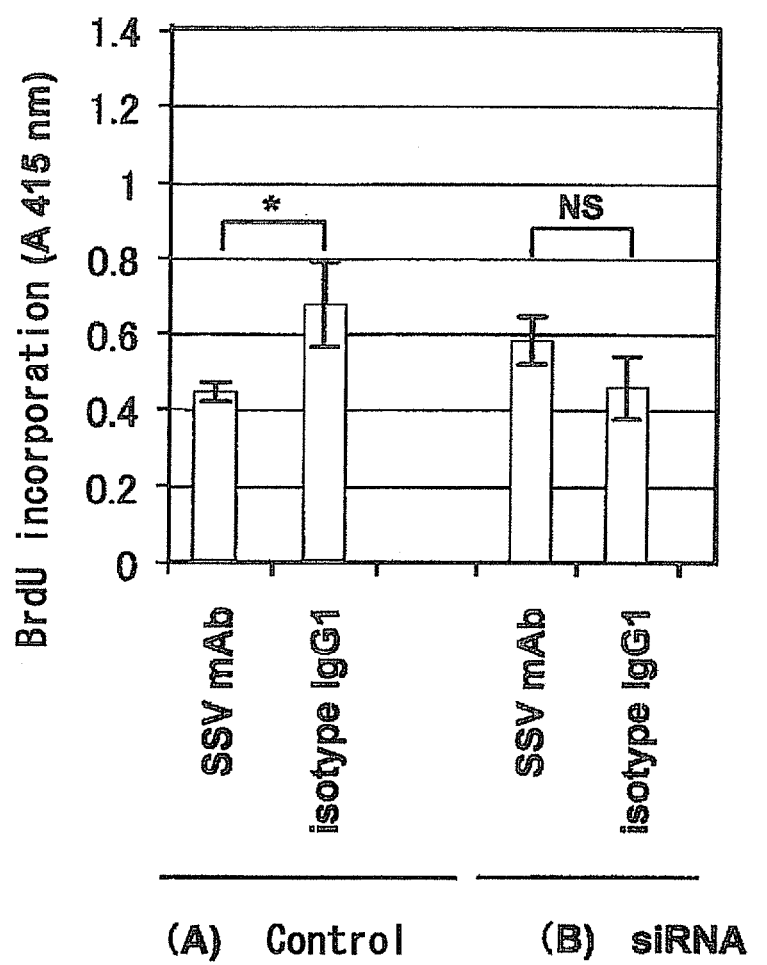
FIG. 6A shows the results from the MLR tests for the monoclonal antibody of the present invention (SSVmAb) and a control reagent (Isotype IgG1) using spleen cells in which ATP synthase is not knocked down by siRNA.
FIG. 6B shows the results of the MLR tests for the monoclonal antibody of the present invention (SSVmAb) and a control reagent (Isotype IgG1) using spleen cells in which ATP synthase is knocked down by siRNA.

The results are shown in FIGS. 6A and 6B.

As shown in FIG. 6A, when the ATP synthase was not knocked down, Example 1 (SSV mAb) significantly inhibited cell growth as compared with Isotype IgG1.

On the other hand, as shown in FIG. 6B, when the ATP synthase was knocked down, no significant difference was observed for cell growth inhibition between Example 1 (SSV mAb) and Isotype IgG1.

FIGS. 6A and 6B suggests that the immunosuppressive activity of SSV mAb is decreased by knocking down the ATP synthase, and that SSV mAb down regulates the activity of the ATP synthase upon immunosuppression.

Test Example 6

Identification of the Sequence for the Variable Regions of the Light and Heavy Chains of SSV mAb Synthesis of Hybridoma cDNA Total RNA was prepared from the $1.6 \times 10^7$ cells of hybridoma obtained in Test Example 1 (Mouse-Mouse hybridoma SSV-C 93-3) using FastPure RNA Kit (TaKaRa). Using Poly (A)$^+$ Isolation Kit from Total RNA (NIPPON GENE), 240 µg of total RNA was prepared from mRNA. Ethanol precipitation was performed using Etachinmate (NIPPON GENE) to precipitate mRNA. After washed with 75% ethanol, mRNA was dried. To this, 10 µL RNase free water was added to dissolve mRNA. The mRNA solution obtained was stored at −80° C. Using SMARTer RACE cDNA Amplification Kit (Clontech), cDNA for 5'-RACE was synthesized from 1 µg SSV hybridoma mRNA. The cDNA solution obtained was stored at −20° C.

Identification of the Complementarity Determining Regions (CDR) in the Light and Heavy Chains of SSV mAb Based on the base sequence of the mouse IgG1 heavy chain constant region, a primer, 5'-CAC CAT GGA GTT AGT TTG GGC AGC AG-3' (SEQ ID NO: 12) was produced. Based on the base sequence of the mouse light K chain constant region, a primer, 5'-CAC GAC TGA GGC ACC TCC AGA TG-3' (SEQ ID NO: 13) was produced. Using a respective primer and Universal Primer A Mix (a primer included in SMARTer RACE cDNA Amplification Kit), 5'-RACE was performed using cDNA as a template. For the RACE reaction, Advantage2 PCR Kit (Clontech) was used. The reaction mixture was subjected to agarose electrophoresis, and a heavy chain 5'-RACE product of about 600 bp and a light chain 5'-RACE product of about 550 bp were purified from the gel using E.Z.N.A. Gel Extraction Kit (OMEGA bio-tek). This was linked to pGEM-T Easy Vector (Promega), with which Competent high E. coli DH5α (TOYOBO) was transformed. From the resulting transformant, the plasmid was prepared using E.Z.N.A. Plasmid Miniprep KitI (OMEGA bio-tek). Using the prepared plasmid as a template, cyclical reactions were performed using BigDye Terminator v3.1 Cycle Sequencing Kit (Applied Biosystems).

Next, the base sequences of the light and heavy chain variable regions were analyzed using a DNA sequencer (Applied Biosystems).

As a result, the base sequence of the light chain variable region was found to be represented by Position 67 to Position 384 of SEQ ID NO: 5.

Further, the base sequence of the heavy chain variable region was found to be represented by Position 58 to Position 423 of SEQ ID NO: 10.

Based on the position of FR (constant region) 1 as determined by the translation initiation codon and the method according to Kabat et al., the followings were estimated: Position 1 to Position 66 of SEQ ID NO: 5 corresponds to the base sequence of the light chain signal peptide, and Position 1 to Position 57 of SEQ ID NO: 10 corresponds to the base sequence of the heavy chain signal peptide.

Next, the amino acid sequences of the variable regions of the light and heavy chains were estimated from the base sequences obtained, and CDR regions was identified in accordance with the method of Kabat et al.

As a result, the amino acid sequence of the light chain variable region was found to be represented by Position 23 to Position 128 of SEQ ID NO: 6. Here, Position 1 to Position 22 of SEQ ID NO: 6 corresponds to the amino acid sequence of the light chain signal peptide.

Further, in the amino acid sequence of the light chain variable region, the followings were determined: CDR1 is represented by RASSSVSYMH (SEQ ID NO: 2), CDR2 is represented by ATSNLAS (SEQ ID NO: 3), and CDR3 is represented by QQWSSNPWT (SEQ ID NO: 4).

Furthermore, the amino acid sequence of the heavy chain variable region was found to be represented by Position 20 to Position 141 of SEQ ID NO: 11. Here, Position 1 to Position 19 of SEQ ID NO: 11 corresponds to the amino acid sequence of the heavy chain signal peptide.

Moreover, in the amino acid sequence of the heavy chain variable region, the followings were determined: CDR1 is represented by GYNMN (SEQ ID NO: 7), CDR2 is represented by NINPYYGSTSYNQKFKG (SEQ ID NO: 8), and CDR3 is represented by SPYYSNYWRYFDY (SEQ ID NO: 9).

What is claimed is:

1. A monoclonal antibody or an antigen binding fragment thereof, which binds to a peptide comprising an amino acid sequence represented by SSVLYGGPPSAA (SEQ ID NO: 1) or a conjugate of the peptide and a pharmaceutically acceptable carrier, the monoclonal antibody or an antigen binding fragment thereof having a higher binding affinity for core histone than for histone H1, wherein the monoclonal antibody or an antigen binding fragment thereof comprises:

a light chain variable region comprising CDR1 consisting of an amino acid sequence represented by RASSSVSYMH (SEQ ID NO: 2), CDR2 consisting of an amino acid sequence represented by ATSNLAS (SEQ ID NO: 3), and CDR3 consisting of an amino acid sequence represented by QQWSSNPWT (SEQ ID NO: 4), and a heavy chain variable region comprising CDR1 consisting of an amino acid sequence represented by GYNMN (SEQ ID NO: 7), CDR2 consisting of an amino acid sequence represented by NINPYYGSTSYNQKFKG (SEQ ID NO: 8), and CDR3 consisting of an amino acid sequence represented by SPYYSNYWRYFDY (SEQ ID NO: 9).

2. The monoclonal antibody or an antigen binding fragment thereof according to claim 1, which is against a peptide consisting of an amino acid sequence represented by SSVLYGGPPSAA (SEQ ID NO: 1) or a conjugate of the peptide and a pharmaceutically acceptable carrier.

3. The monoclonal antibody or an antigen binding fragment thereof according to claim 1, wherein the light chain variable region of the monoclonal antibody or an antigen binding fragment thereof comprises an amino acid sequence represented by Position 23 to Position 128 of SEQ ID NO: 6.

4. The monoclonal antibody or an antigen binding fragment thereof according to claim 1, wherein the heavy chain variable region of the monoclonal antibody or an antigen binding fragment thereof comprises an amino acid sequence represented by Position 20 to Position 141 of SEQ 1 D NO: 11.

5. The monoclonal antibody or an antigen binding fragment thereof according to claim 1, which down-regulates an ATP synthase activity.

6. The monoclonal antibody or an antigen binding fragment thereof according to claim 1, wherein the monoclonal antibody is a chimera or humanized antibody.

7. The monoclonal antibody or an antigen binding fragment thereof according to claim 1, wherein the core histone is at least one selected from histone H2A, H2B, H3 and H4.

8. The monoclonal antibody or an antigen binding fragment thereof according to claim 1, wherein the pharmaceutically acceptable carrier is keyhole limpet hemocyanin, ovalbumin or bovine serum albumin.

9. The monoclonal antibody or an antigen binding fragment thereof according to claim 1, wherein the antigen binding fragment is Fab, Fab', (Fab')$_2$, Fv or scFv.

10. A pharmaceutical composition comprising the monoclonal antibody or an antigen binding fragment thereof according to claim 1.

* * * * *